(12) United States Patent
Wolf et al.

(10) Patent No.: US 6,731,385 B1
(45) Date of Patent: May 4, 2004

(54) PRESSURE-PROOF PROCESS WINDOW

(75) Inventors: Udo Wolf, Kempen (DE); Lutz Spauschus, Kerken (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/937,409

(22) PCT Filed: Mar. 14, 2000

(86) PCT No.: PCT/EP00/02239

§ 371 (c)(1),
(2), (4) Date: Sep. 24, 2001

(87) PCT Pub. No.: WO00/58711

PCT Pub. Date: Oct. 5, 2000

(30) Foreign Application Priority Data

Mar. 26, 1999 (DE) .......................... 199 13 730

(51) Int. Cl.[7] .......................... G01N 21/47; G01N 21/00
(52) U.S. Cl. ....................... 356/246; 356/244
(58) Field of Search ................. 356/244, 246; 73/334; 220/327, 328

(56) References Cited

U.S. PATENT DOCUMENTS

| | | | |
|---|---|---|---|
| 3,886,364 A | * | 5/1975 | Walker et al. .............. 250/343 |
| 4,575,869 A | * | 3/1986 | Torrisi et al. ................. 378/47 |
| 4,738,064 A | * | 4/1988 | Aarts et al. ................. 52/204.5 |
| 4,910,403 A | * | 3/1990 | Kilham et al. .............. 250/343 |
| 5,003,174 A | * | 3/1991 | Datwyler et al. ........... 250/343 |
| 5,062,706 A | * | 11/1991 | Magnussen, Jr. ............ 356/246 |
| 5,151,474 A | | 9/1992 | Lange et al. ................. 526/60 |

FOREIGN PATENT DOCUMENTS

| EP | 0 493 746 | 7/1992 |
|---|---|---|
| FR | 2067407 | 3/1991 |

* cited by examiner

Primary Examiner—Rodney Fuller
(74) Attorney, Agent, or Firm—Joseph C. Gil; Gary F. Matz

(57) ABSTRACT

A pressure-resistant process window (1) for visual or spectroscopic examinations of pressurized products in pipes and reactors. The process window (1) consists of at least a measurement-cell body (2), which is connected to the pipe or the reactor, and a transparent window pane (3), a seal (4) between the measurement-cell body (2) and the window pane (3) for sealing the reactor or pipe interior off from the environment, where the window pane (3) is held against the measurement-cell body (2) in a sealing manner by use of a screw barrel (5) having an external thread (6), which can be screwed into a hollow barrel (7) with internal thread (8) which is connected to the measurement-cell body (2).

8 Claims, 4 Drawing Sheets

PRESSURE-PROOF PROCESS WINDOW

This application is the National Stage Application of PCT/EP00/02239, which claims a priority from German Application 199 13 730.7 filed Mar. 26, 1999.

BACKGROUND

The invention relates to a pressure-resistant process window for in-process, monitoring for visual or spectroscopic investigation of pressurized products in pipes and reactors. The process window consists at least of a measurement-cell body connected to the pipe or the reactor, and a transparent window pane, a seal between the measurement cell body and a window pane for sealing the reactor or pipe interior off from the environment, where the window pane is held against the measurement-cell body in a sealing manner by means of a screw barrel with an external thread which can be screwed into a hollow barrel with internal thread which is connected to the measurement-cell body.

Chemical production processes can be controlled efficiently if the current composition or quality of the product or of a reaction mixture is known at various stages of the production process. The requisite quality-relevant parameters can be determined with the aid of continuous on-line methods.

A particular key position in the determination of these parameters is held by spectroscopic methods, since these are able to determine current product properties without complex modification or treatment of the product being necessary.

The usual spectroscopic methods in this connection are UV/VIS spectroscopy (measurement of the absorption of the product in the wavelength range $\lambda=200–800$ nm), NIR spectroscopy (measurement of the absorption of the product in the wavelength range $v=800–2500$ nm), IR spectroscopy (measurement of the absorption of the product in the wave number range $v=4000–400$ cm$^{-1}$) and fluorescence and Raman spectroscopy (excitation of fluorescence or Raman radiation by means of intense light sources).

An essential prerequisite for the usability of these methods is access to the process or product to be examined. Chemical processes are generally carried out in reaction tanks or pipes, which only allow spectroscopic measurement of the product therein after installation of windows which are transparent to the spectroscopic analysis radiation.

Due to possible toxic properties of the products to be analyzed in the process, high demands must be made of the reliability of process windows with respect to the leaks. This also applies in particular if processes are carried out under high pressure or high temperature.

Process windows of this type are available, for example, as inspection glasses. Inspection glasses are designed principally for visual monitoring of the reactor or pipe contents, less for spectroscopic process applications, in which a layer thickness, adjustable in a defined manner, of a product through which radiation is to be passed is required so that the desired product information can be derived from the spectrum.

Process windows for spectroscopic applications as part of an in-line measurement cell are described in the brochure from Optec-Danulat GmbH, D-45143, Essen, In-line photometry system overview 4.0, page 9 (corresponding to German Utility Model G 87 17 609.2). In these, stepped windows made of Pyrex or sapphire are pressed by means of a window ring against the window in contact with the product, which is sealed off from the product to be analyzed by means of an O-ring. The window ring is screwed to the measurement cell 1 by means of four screws. The pressure resistance of this known process window is essentially determined by the tensile strength and stripping force of the four clamping screws. The pressure resistance of this process window is inadequate for many potential applications.

A further process window is from U.S. Pat. No. 4,910,403. Here, a diamond window is soldered to a support which can be screwed in. This is designed, in particular, to be screwed into a standard pressure sensor port of an extruder. The typical diameter of the diamond window is 4.25 mm. If higher optical throughput is to be facilitated, the diameter of the diamond window has to be increased, which can result in very high material costs. A further disadvantage is the higher number of sealing surfaces required.

A sapphire window which has been soldered into a support is described analogously in the patent U.S. Pat. No. 5,151,474 of The Dow Chemical Company. Here too, it is problematic to implement greater diameters of the sapphire window in order to achieve higher optical throughput, since the soldering process is ever more difficult to carry out with increasing diameter. The unsatisfactory chemicals resistance of the solder to aggressive acids or lyes can also make the use of this technique for monitoring chemical processes impossible.

The object of the invention was to develop a process window which does not have the design disadvantages of the known arrangements, and in particular exhibits high pressure resistance and freedom from leaks over an extended operating period.

DESCRIPTION

The object is achieved by a pressure-resistant process window for visual or spectroscopic,examination of pressurized products in pipes and reactors, which is the subject-matter of the invention, consisting at least of a measurement-cell body connected to the pipe or the reactor, and a transparent window pane, a seal between the measurement-cell body and a window pane for sealing the reactor or pipe interior off from the environment, characterized in that the window pane is held against the measurement-cell body in a sealing manner by means of a screw barrel with an external thread which can be screwed into a hollow barrel with internal thread which is connected to the measurement-cell body.

A preferred embodiment of the process window is designed in such a way that the hollow barrel has an annular sealing surface on which the window pane lies in a pressure-tight manner.

A particularly pressure-stable embodiment of the process window is designed in such a way that the hollow barrel is formed in one piece with the measurement-cell body or is welded thereto.

In a prefer variant of the process window, the hollow barrel is connected to the measurement-cell body in a pressure-resistant and detachable manner.

The process window may be designed in such a way that a ring of low friction to the barrel or the window pane is present between the screw barrel with external thread and the window pane and facilitates a pressure-resistant screw connection which is gentle on the window pane.

The window pane of the process window preferably has a greater wall thickness in the central region. This results in the formation of a bearing surface for, for example, ring seals. In addition, the reduction in the size of the side of the window pane in contact with the product achieves a reduction in the dead space (between the pipe wall and the window pane).

The ring between the screw barrel with external thread and the window pane preferably consists of graphite.

In a preferred variant of the process window, two rings which are in sliding contact with one another are present instead of a ring with low friction between the screw barrel with external thread and the window pane.

Examples of suitable materials for the transparent window pane are the materials which are basically known for the production of inspection glasses or spectroscopic windows, such as borosilicate glass, quartz or sapphire, which exhibit no or low absorption in the region of the typical relevant wavelengths mentioned at the outset for optical spectroscopy. In the case of glass, they can be produced in accordance with DIN 7080, 7081, 8902 and 8903 standards, so that they have official approval for the selected pressure range in accordance with the pressure container regulation (AD-N4). Such glasses are described, for example, in the brochure of "Technische Glaswerke Ilmenau GmbH", D 98684 Ilmenau.

The use of the process window is possible, without any claim to completeness, for the spectroscopic or visual determination of the chemical composition, substance identity, mixture analysis, purity of the substances flowing through the pipe or the reactor, and characteristic numbers, such as, for example, OH and acid numbers (NIR spectroscopy), for the determination of colour (VIS spectroscopy), for the determination of particle impurities or solids contents (scattered-light measurements) or for the visual inspection of the substances (with the eye or by means of a camera.

In the case of transmitted radiation measurement through a pipe, two of the windows according to the invention are installed opposite one another. It may then be necessary to increase the thickness of the installed window panes to the inside in order to reduce the absorption of the measurement radiation by the product.

Materials which are basically suitable for the window pane for the UV (200–400 nM), visible (400–800 nm), near infrared (800–2500 nm) and infrared (4000–400 cm$^{-1}$) spectral region are described in the book Bauelemente der Optik [Optical Components], 5$^{th}$ Edition by G. Schröder, Hanser-Verlag 1987, ISBN 3-446-14960-0.

For use in the UV spectral region, emphasis should be placed on materials such as quartz, Suprasil quartz glass and sapphire, and the speciality glasses from Schott FK 5, UBK 7, UK 50 and BaK 2 (Schott Glaswerke, Hattenbergstraβe 10, Mainz: optical glass, glass mouldings, radiation-protection glasses and windows).

Preferred window materials for use in the visible spectral region are sapphire, quartz, Pyrex glass and zirconium dioxide.

Preferred window materials for use in the near infrared spectral region are sapphire, zirconium dioxide and quartz.

Preferred window materials for use in the IR spectral region are zinc sulphide (ZnS), zinc selenide (ZnSe) and germanium (Ge).

Basically, all window materials are suitable which have adequately high transmission, strength, heat and chemicals resistance in the specific application.

The seals used for the process window can be either flat seals or O-ring seals.

The O-ring seal is preferably not located in an annular groove (for manufacturing au regions), but in a turned-out projection of the measurement-cell body. The depth of the projection is less than the diameter of the O-ring, and the width of the projection is greater than the diameter of the O-ring. By pressing the window against the O-ring or against the measurement-cell body with the aid of the screw barrel, a prestressing of the O-ring which is necessary for the correct sealing function is generated.

On use of flat seals, a groove is usually not provided. For fixing of the seal, a narrow and flat concentric groove or a narrow and flat turned-out projection can be worked into the measurement-cell body. The window is pressed against the seal with the aid of the screw barrel.

The choice of sealing material depends on the thermal and chemical load. In particular, use is made of elastic plastics, moulding compositions comprising inorganic fibres and binders, graphite and deformable metals, for example soft copper.

Proven flat-seal materials are:

PTFE (filled or unfilled, solid material or expanded material (Gore-Tex) with the advantage of very good chemicals resistance and heat resistance up to about 260° C.

Graphite seals with metal inlay or without inlay (for example HDF-Flexitallic GmbH) with the advantage of heat resistance up to about 480° C.

Proven seal materials are fluorinated elastomers, such as, for example, Kalrez® (manufacturer: DuPont de Nemour) and Viton® (manufacturer: DuPont de Nemour) and nitrile rubber or silicone rubber.

Instead of a sliding ring, it is also conceivable to use two rings which are in sliding contact with one another, in particular a so-called axial pressure bearing (ball or roller bearing).

The process windows according to the invention can also be installed in pairs opposite one another on a pipe.

This enables radiation to pass through a product in the pipe, for example for transmission measurements.

The invention furthermore relates to the use of the process window according to the invention for optical or spectroscopic process control, in particular of chemical reactions, and of mixing, conveying and separation processes.

The invention is explained in greater detail by way of example below with reference to the figures, without thereby restricting the invention in detail.

THE FIGURES SHOW THE FOLLOWING

FIG. 1b shows the plan view of the known process window according to FIG. 1a.

FIG. 2b shows the plan view of the process window according to the invention according to FIG. 2a.

FIG. 3b shows the plan view of the process window according to FIG. 3a.

FIG. 4b shows the plan view of the process window according to FIG. 4a.

Figure 1A:
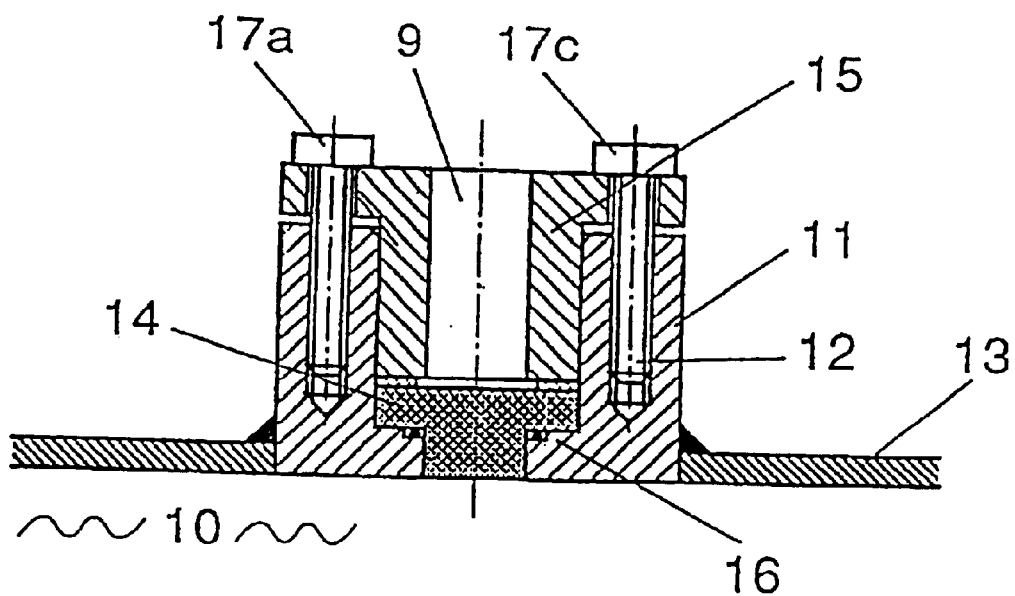
FIG. 1a shows the simplified diagrammatic cross-sectional representation of a conventional process window.

The invention is further described in the following illustrative examples.

EXAMPLES

Example 1

Comparative Example

A conventional process window has the following structure: The accommodation bush 11 with the threaded holes 12 is welded into a pipe 13. The window pane 14 is pressed against the ring seal 16 by means of a pressure sleeve 15. The pressing pressure is generated by means of four threaded screws 17a to 17d, which are screwed into the threaded holes 12.

Figure 1B:
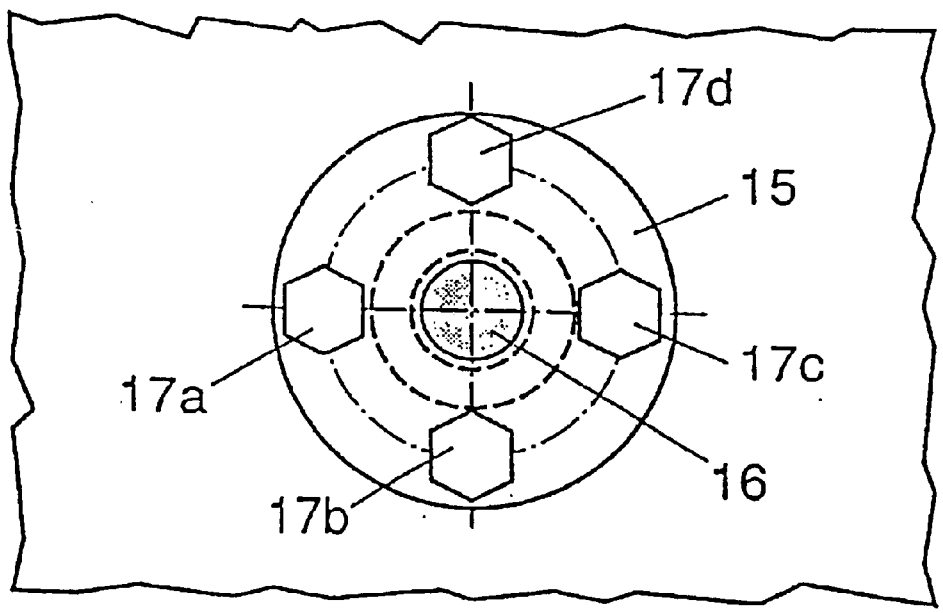

In the case of this example which is not according to the invention (FIGS. 1a and 1b), the pressure resistance is determined essentially by the tensile strength and stripping force of the four threaded screws 17a to 17d. The pressure resistance of the arrangement has been calculated by means of the DIMY 4.00/Rev 3 module FESTFL 4.00 computer program from RW TÜV Essen. If four M5 screws are used, the pressure resistance is a maximum of about 15 bar, while if M6 screws are used, it is correspondingly a maximum of 42 bar. The pressure resistance is thus inadequate for many potential applications.

Example 2

Figure 2A:
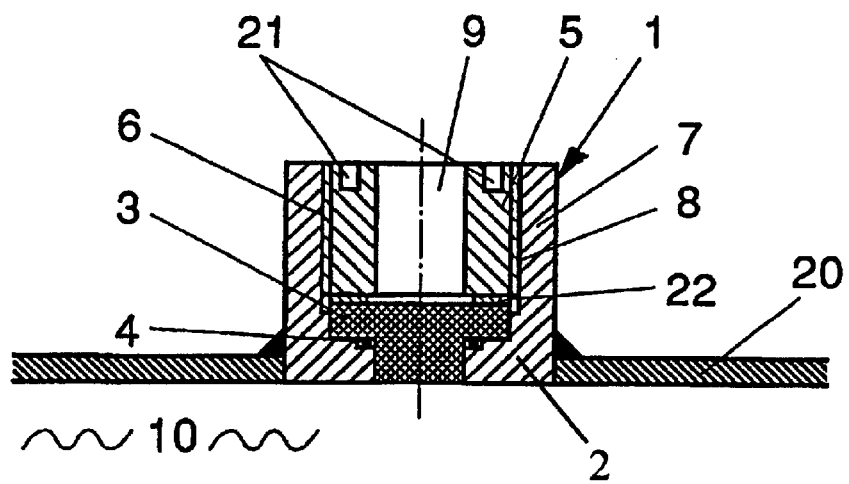
FIG. 2a shows the simplified diagrammatic cross-sectional representation of a process window according to the invention.
Figure 2B:
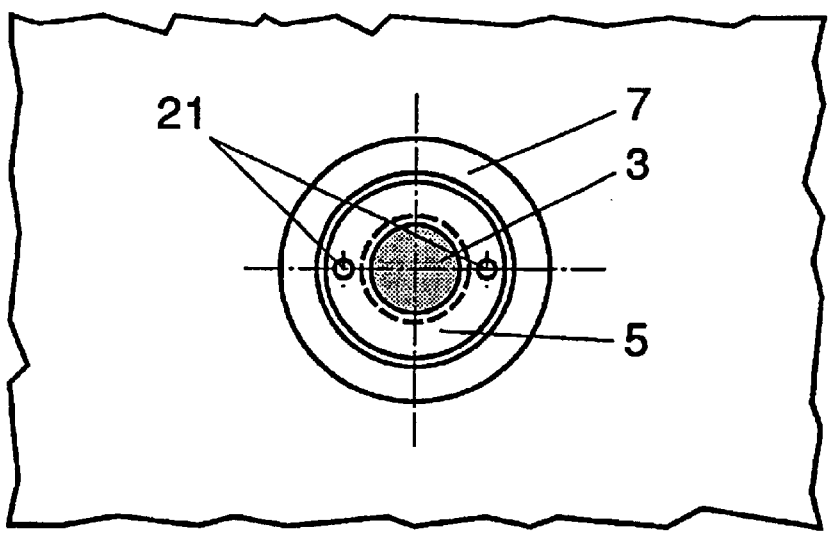

In a process window 1 according to FIGS. 2a and 2b, the accomodation sleeve 7 with the internal thread 8 is welded into a pipe 20 above the measurement-cell body 2. A screw-in sleeve 5, which has an external thread 6, is screwed into the accomodation sleeve 7. The screw-in sleeve 5 has holes 21 in the head part, into which pegs of an Allen key (not shown) are able to engage for screwing together. The screw-in sleeve 5 has a planar surface on its underside, which is in contact with the window pane 3. The window pane 3 is in the design according to the invention (FIGS. 2a and 2b) pressed by means of the screw-in sleeve 5 via a ring seal 22 against a seal 4, which sits in an annular groove in the lower, projecting part of the accomodation sleeve 7 and seals the interior 10 of the pipe 20 off against the environment.

The pressure resistance of the pressure window resulting from the stripping force of the screw-in sleeve 5 has been estimated at 1300 bar. The pressure resistance of the process window can itself, if sapphire is used as the material for the window pane, be estimated at about 450 bar. The window pane 3 here has in cross section (FIG. 2a) a thickness of 11 mm in the thinner, outer region and a thickness of 16 mm in the thicker, inner region.

The advantage of the design according to the invention over the example which is not according to the invention lies in the significantly greater pressure resistance in combination with reduced dimensions of the measurement channel and reduced weight. This results firstly in easier integration of process windows into existing pipes, and improved optical properties are achieved through the length/diameter ratio of the measurement channel 9 being reduced compared with the known arrangement (Ex. 1).

Figure 3A:
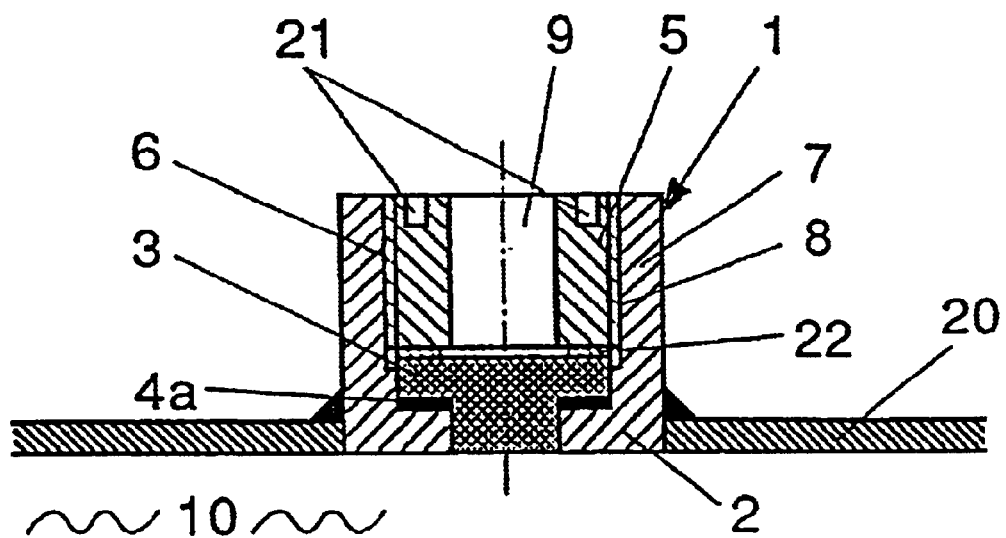
FIG. 3a shows a variant of the arrangement according to FIG. 2a with sliding-ring seal.
Figure 3B:
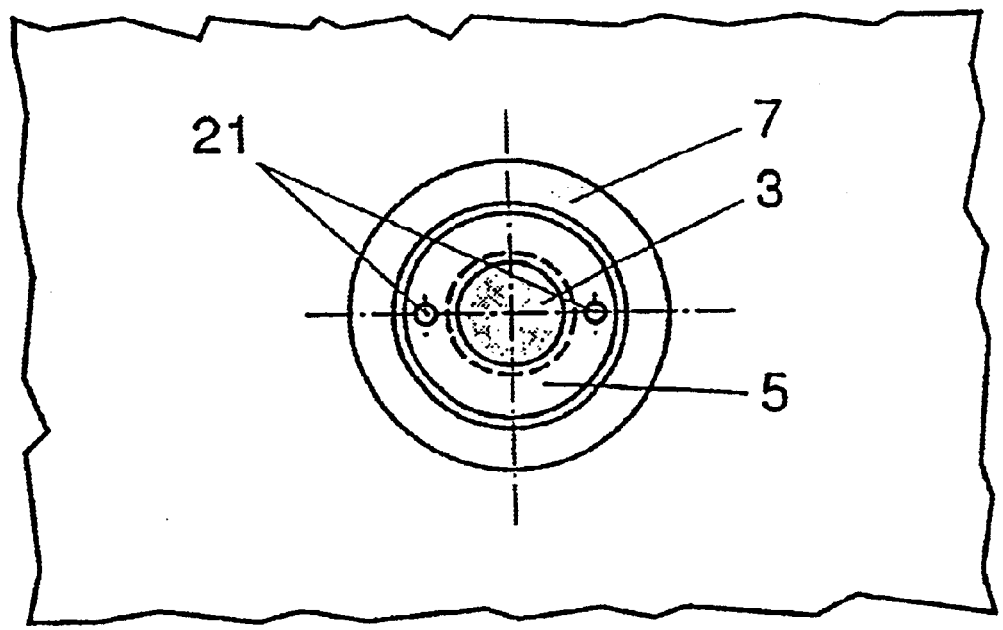

FIGS. 3a and 3b show views of a process window of basically the same design as in FIGS. 2a, 2b, but in which the O-ring seal 4 with annular groove has been replaced by a sliding-ring seal with sliding surface.

Figure 4A:
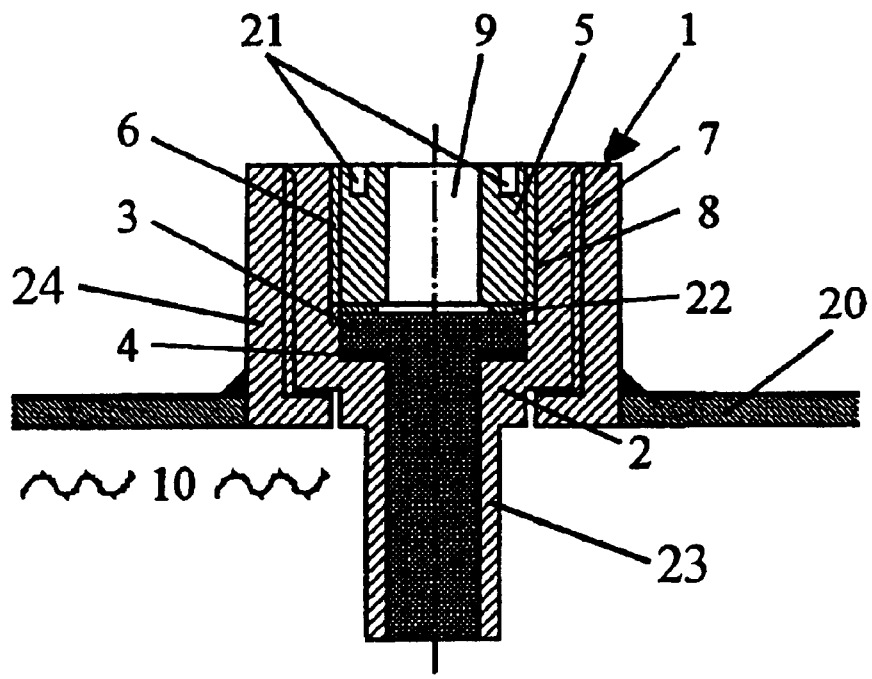
FIG. 4a shows a variant of the process window according to FIG. 2a with extended transmitted-radiation region of the window.
Figure 4B:
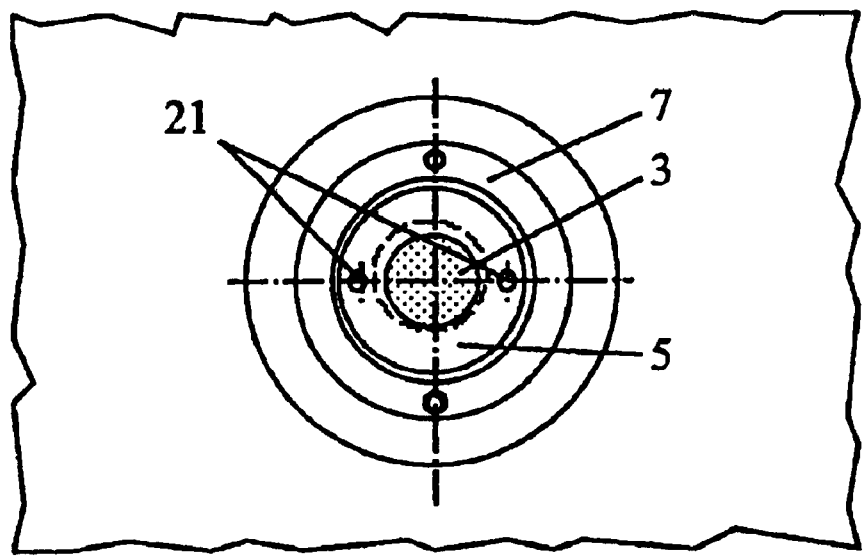

FIGS. 4a and 4b show in addition a further variant which can be used in flowing media of high viscosity (polymer melts). The sapphire window 3 here projects well to the inside so that the layer thickness of the product through which radiation passes is reduced. A steel sleeve 23 at the side ensures that the sapphire window cannot break out. The accommodation sleeve 7 and measurement-cell body here are designed in two parts, so that the inner steel sleeve 7 and the measurement-cell body 2 can be screwed out of the outer steel sleeve 24 together with the window 3.

The particular advantage of this variant is that the window 3, for example after surface soiling, can be exchanged by screwing it out together with the steel sleeve 2, 7, 23, which is preferably designed in one piece. The outer steel sleeve 24 is welded to the pipe.

In another variant, the window has to be pressed from the inside outward after screwing-out of the screw-in sleeve 5. However, this is not possible if the window has been installed in a continuous, relatively long piece of a pipe.

Although the present invention has been described in detail with reference to certain preferred versions thereof, other variations are possible. Therefore, the spirit and scope of the appended claims should not be limited to the description of the versions contained therein.

What is claimed is:

1. A pressure resistant process window for visual or spectroscopic examination of pressurized products in a pipe or a reactor comprising:

(A) at least one measurement-cell body that is connected to a pipe or a reactor, and a transparent window pane having (i) a central region, (ii) an outer region, and (iii) a wall thickness in the central region that is greater than a wall thickness in the outer region, wherein the window pane is sealed against the measurement-cell body with a screw barrel having an external thread that can be screwed into a hollow barrel that (a) has an internal thread that is connected to the measurement-cell body, and (b) is connected to the measurement-cell body in a pressure-resistant or in a pressure-resistant and detachable manner; and (B) a seal between the measurement-cell body and the window pane for sealing the reactor interior or pipe interior from surroundings of the reactor interior or pipe interior.

2. The process window according to claim 1, wherein the hollow barrel has an annular sealing surface on which the window pane contacts in a pressure-resistant manner.

3. The process window according to claim 1, wherein the hollow barrel is designed in one piece with the measurement-cell body or is welded thereto.

4. The process window according to claim 1, wherein the hollow barrel is connected to the measurement-cell body in a pressure-resistant, detachable manner.

5. The process window according to claim 1, wherein a ring with low friction against the barrel or the window pane is present between the screw barrel and the window pane.

6. The process window according to claim 5, wherein the ring is graphite.

7. The process window according to claim 5, wherein two rings which are in sliding contact with one another are present instead of a ring.

8. The process window according to claim 1, wherein the window pane extends into the pipe or the reactor with the central region and is surrounded on its periphery by a protective sleeve.

* * * * *